United States Patent
Rampy et al.

[11] Patent Number: 5,646,736
[45] Date of Patent: Jul. 8, 1997

[54] ANALYTICAL APPARATUS WITH CODED ELEMENTS

[75] Inventors: Gordon A. Rampy, Warrenton, Va.; Rame Bull, Schaumburg, Ill.; Henry Castañeda, Woodbridge, Va.; Teresa A. Neale, Bealeton, Va.; G. Neil Spokes, Marshall, Va.; Edgar Watson, Jr., Grayslake, Ill.

[73] Assignee: CHEMetrics, Inc., Calverton, Va.

[21] Appl. No.: 574,515

[22] Filed: Dec. 19, 1995

[51] Int. Cl.$^6$ .................................................. G01N 21/25
[52] U.S. Cl. .................................................. 356/419
[58] Field of Search ............................ 356/402–411, 323, 356/319, 320, 321, 324, 325, 326, 414–416, 417–420, 436, 51, 39, 432–434, 440–442, 244, 246; 422/62–63, 67, 68.1, 82.05, 82.08, 82.09; 436/50, 164, 165, 171; 235/468

[56] References Cited

U.S. PATENT DOCUMENTS

| | | |
|---|---|---|
| 3,634,038 | 1/1972 | Rampy . |
| 3,704,953 | 12/1972 | Carter et al. . |
| 3,831,006 | 8/1974 | Chaffin, III et al. . |
| 4,012,287 | 3/1977 | Carl et al. . |
| 4,055,752 | 10/1977 | Kappe et al. . |
| 4,163,643 | 8/1979 | Hunter et al. . |
| 4,338,396 | 7/1982 | Kiyasu . |
| 4,431,924 | 2/1984 | Suovaniemi et al. . |
| 4,460,824 | 7/1984 | Kadogaki . |
| 4,476,016 | 10/1984 | Kiyasu . |
| 4,497,898 | 2/1985 | Anderson et al. . |
| 4,528,159 | 7/1985 | Liston . |
| 4,762,420 | 8/1988 | Bowley . |
| 4,843,021 | 6/1989 | Noguchi et al. . |
| 4,863,690 | 9/1989 | Berthold et al. . |
| 4,877,134 | 10/1989 | Klein . |
| 4,935,875 | 6/1990 | Shah et al. . |
| 4,980,292 | 12/1990 | Elbert et al. . |
| 5,009,316 | 4/1991 | Klein . |
| 5,084,041 | 1/1992 | Oxley et al. . |
| 5,096,670 | 3/1992 | Harris et al. . |
| 5,128,103 | 7/1992 | Wang et al. . |
| 5,160,329 | 11/1992 | Oxley . |
| 5,166,498 | 11/1992 | Neeley . |
| 5,217,443 | 6/1993 | Oxley . |
| 5,236,666 | 8/1993 | Hulette et al. . |
| 5,254,473 | 10/1993 | Patel . |
| 5,284,772 | 2/1994 | Oxley . |
| 5,386,287 | 1/1995 | Berssen et al. . |
| 5,526,121 | 6/1996 | Sandifer et al. ............ 356/418 |

*Primary Examiner*—K. Hantis
*Attorney, Agent, or Firm*—Dickinson, Wright, Moon, Van Dusen & Freeman

[57] ABSTRACT

An instrument kit includes a photometric instrument and a standardizing ampoule. The standardizing ampoule includes a machine readable code that is recognized by the instrument when the ampoule is inserted to initiate a standardizing routine. An analysis kit includes an optical filter assembly and a sample ampoule to be used with the instrument. The filter assembly also includes a machine readable code that is detected by the instrument when inserted to identify the particular test to be conducted by the instrument. The instrument automatically applies the relationship between detected light and concentration of a substance for the particular test and displays the sample concentration in numeric digital form. The instrument operates automatically, and there are no buttons or other external input devices.

12 Claims, 2 Drawing Sheets

ANALYTICAL APPARATUS WITH CODED ELEMENTS

TECHNICAL FIELD

This application relates to an apparatus for measuring the concentration of chemicals in aqueous solution. In particular, the invention includes a photometer kit and a chemical analysis kit. The chemical analysis kit includes an optical filter and a reagent ampoule designed specifically for use with the photometer. The photometer kit includes a photometer and a zeroing ampoule.

BACKGROUND ART

Photometers for performing analytical measurements are known. One such instrument is described in U.S. Pat. No. 3,704,953 (Carter et al.). The instrument shown in that patent includes a spectrophotometer that can be programmed to detect light of selected wavelengths. Samples to be analyzed are held in containers that have optically readable codes thereon. The instrument reads the code on the sample container as it is loaded into the spectrophotometer, the particular code being representative of the test to be conducted on that sample. The spectrophotometer then scans the wavelengths necessary to conduct the particular test and records the results.

Instruments of the type shown in the Carter patent are, typically, complicated laboratory instruments that are not easily carried into the field for use.

SUMMARY OF THE INVENTION

A photometric instrument in accordance with the invention offers remarkable ease of use either by highly skilled or unskilled staff. The unit is portable to allow advantageous use both in the field and in the laboratory. Additionally, it permits a wide variety of tests to be performed on aqueous samples. The instrument is used in conjunction with an analysis kit that is specifically designed for use in conducting a particular test. The kit includes an optical filter element and a reagent ampoule containing pre-loaded reagents dictated by the test to be performed. The filter is in a holder that is provided with a machine-readable code representative of the test to be conducted by the instrument. The code is read by the instrument when the filter assembly, which includes the holder and the filter element, is inserted into a receptacle in the instrument at the beginning of the test. The instrument is programmed to recognize the filter code and to perform the corresponding test. For example, if the code corresponds to a test for copper, the instrument will use the internally-recorded relationship between detected light intensity and copper concentration in a sample to determine the concentration of copper in a particular sample and will display the results in digital numeric form. (The term "light" as used herein refers generally to radiation used for absorption or reflection testing and is not limited to visible frequencies.) Each of the receptacles includes a switch that is closed when a filter assembly or a sample ampoule is inserted. The switches are part of the instrument's electronic circuit and cause the instrument to be activated when both of these items are properly inserted. In the preferred embodiment, each of the switches is a leaf switch located at the bottom of a respective receptacle.

The instrument kit includes the instrument itself and a standardizing ampoule that is used before the tests are conducted. The standardizing ampoule contains a code that is read by the instrument when it is placed in the ampoule receptacle. The instrument recognizes the standardizing ampoule by the code and performs a standardizing routine that is known in the art.

The analysis kit includes analytical test ampoules as described in U.S. Pat. No. 3,634,038 and accessory chemicals that may be added to a liquid sample. The sample is placed in a sample cup, and the ampoule is immersed, tip down, in the sample in the cup. The tip of the ampoule is then broken off, and because the pressure in the ampoule is less than atmospheric, the sample is drawn into the ampoule. The sample is then mixed with chemicals contained in the ampoule for use in the photometric test.

A particular advantage of Applicants' instrument lies in its lack of "buttons" or other external controls, resulting from automatic recognition of the filter code and automatic activation upon insertion of the filter assembly and ampoule. This feature obviates the necessity of data entry by the operator, which simplifies use and precludes entry of erroneous data.

An object of this invention is to provide an analytical instrument that is easy to use by skilled and unskilled operators.

Another object of this invention is to provide an analytical kit that, when associated with an analytical instrument of the invention, provides easy analysis of the aqueous concentration of a selected one of a wide variety of chemicals.

BRIEF DESCRIPTION OF THE DRAWINGS

FIG. 3b is a side view of the filter assembly of FIG. 3a.

DETAILED DESCRIPTION OF THE PREFERRED EMBODIMENT

Figure 1:
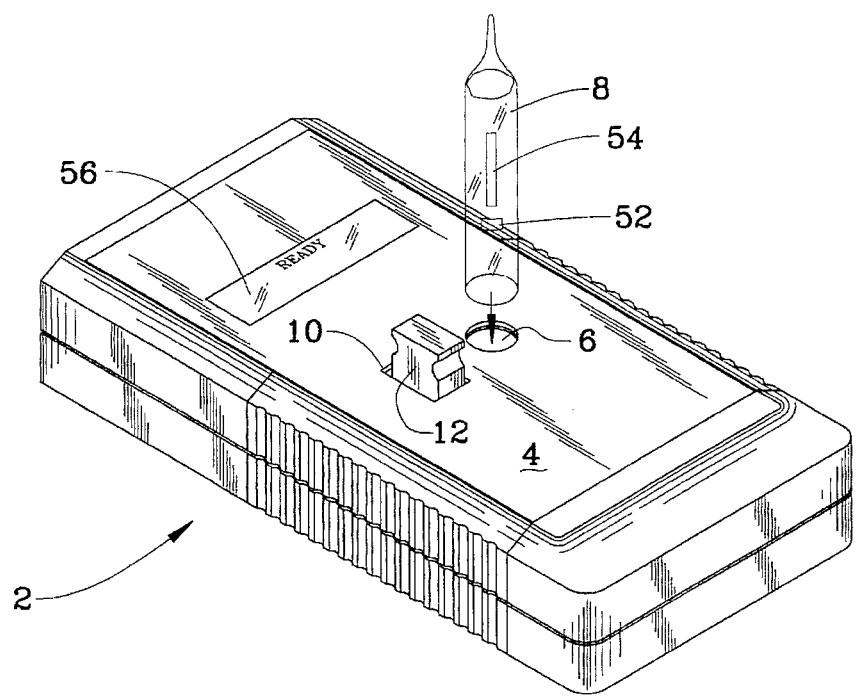
FIG. 1 is a perspective of a preferred embodiment of an instrument in accordance with the invention.
Figure 2:
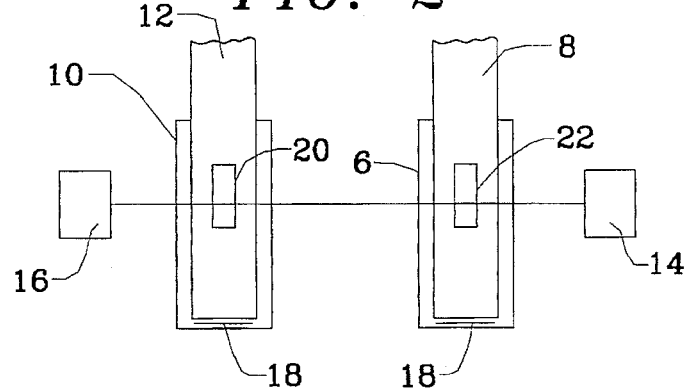
FIG. 2 is a schematic portrayal of the instrument's optical system.

With reference to FIG. 1 of the drawings, a photometric instrument 2 in accordance with the invention includes a housing 4. The housing forms a sample receptacle 6 for receiving a removable ampoule 8 for analysis. The housing also provides a receptacle 10 for receiving a removable filter assembly 12. As illustrated in FIG. 2, the instrument internally includes a light source 14 and a photo detector 16, which define a light path. The ampoule sample receptacle 6 and filter receptacle 10 are located in that light path so that the ampoule 8 and filter assembly 12 lie in the light path in a known manner when they are placed in their respective receptacles. Each of the receptacles 6 and 10 also includes a switch 18 for determining whether an ampoule or filter assembly is in the receptacle. The switch may be either mechanical or electronic and is preferably a leaf switch at the bottom of each receptacle. The instrument circuitry (not shown) is activated only when the switches are closed, which eliminates the necessity of an on/off switch to be activated by the user.

A code reader 20 is adjacent the filter receptacle 10 to read a code on the side of a filter holder when placed in the filter receptacle. Similarly, a code reader 22 is adjacent the sample receptacle to read the code on the ampoule when it is in the sample receptacle. In the preferred embodiment, however, only the standardizing ampoule is provided with such a code. The sample ampoules need not be coded because they are part of the kit that includes a filter assembly that uniquely identifies the test to be conducted. In addition, the sample ampoules are contained within the kit in a box marked with the particular test.

The code readers 20 and 22 are preferably commercially available infrared reflection devices. Code reader 22 may be a single-station reader, while code reader 20 is preferably a six-station reader.

A microprocessor (not shown) is also provided in the instrument housing. The microprocessor is programmed to include in its memory the relationship between the output of a photocell and the sample concentration for each of several substances the instrument is designed to analyze. The microprocessor is also programmed to determine the concentration of a particular chemical in a sample by comparing in known fashion the actual electronic output from the photo detector with the particular one of these relationships identified by the code on the particular filter assembly. The output of the microprocessor is then supplied to the numeric digital display 56 for observation by the user.

Figure 3A:
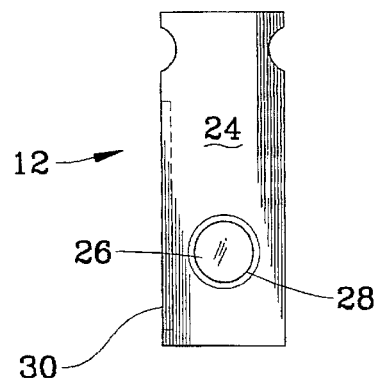
FIG. 3a is a from view of a filter assembly for use with the instrument of FIG. 1.
Figure 3B:
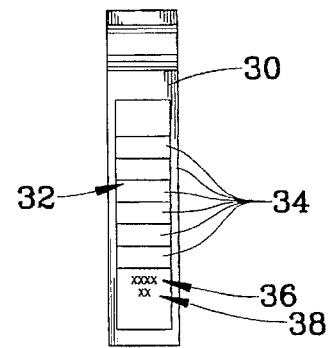

A preferred form of the filter assembly is shown in FIGS. 3a and 3b. The filter assembly comprises a holder, or frame, 24 that supports a filter element 26, e.g., an interference filter. The filter element is viewable through a window 28, which is aligned with the light path from the source 14 when the filter assembly is inserted in the receptacle 10. One side 30 of the filter holder 24 includes a code 32 formed by a plurality of bars 34. In the preferred embodiment, the code is a 6-bit code formed by light or dark bars 34. The side of the holder additionally includes a part number code 36 and an analyte code 38, which are manually readable, for quality control purposes. These codes may be placed on other surfaces of the filter holder, and in the preferred embodiment are on a label affixed to the holder.

Figure 4:
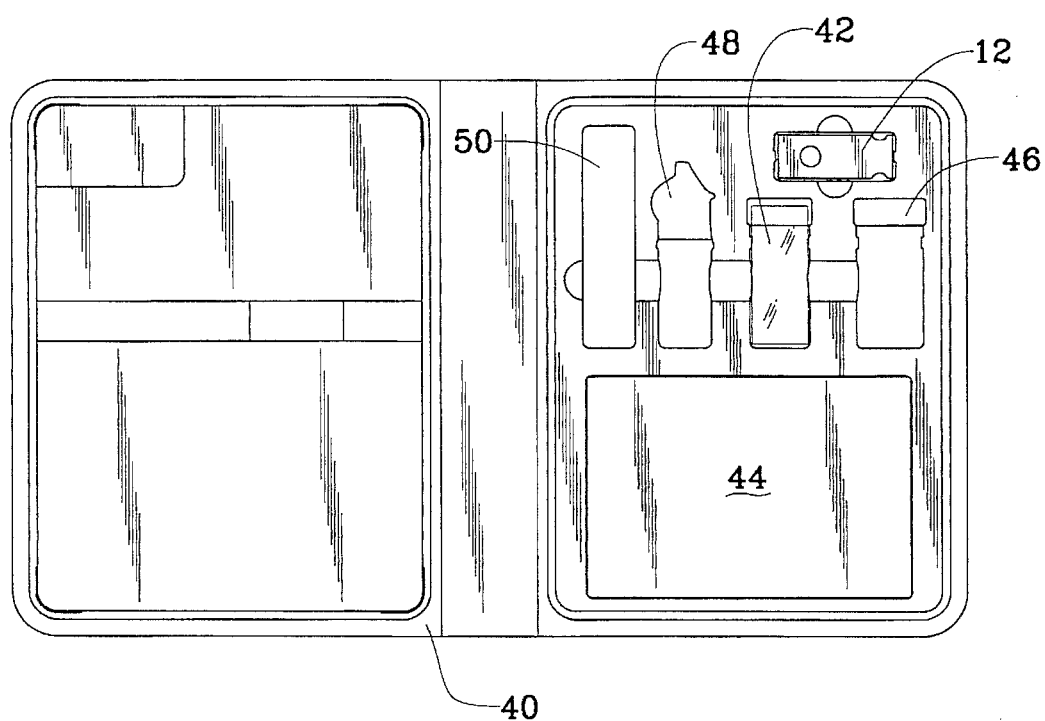
FIG. 4 is a perspective of an analysis kit for use with the instrument of FIG. 1.

A preferred form of an analysis kit for use with the instrument is illustrated in FIG. 4. This kit includes a folding case 40 for holding items necessary to conduct a particular chemical analysis. The case, thus, includes a particular filter assembly 12 bearing a code indicative of the test to be performed. A sample cup 42 is provided for receiving the liquid sample to be tested. A plurality of sample ampoules 8 is provided in compartment 44. In the preferred embodiment, the sample ampoules do not include machine readable codes such as that used on the standardizing ampoules, to reduce inventory costs. Additional chemicals as may be required for the tests are provided in containers 46, 48, or 50.

Figure 5:
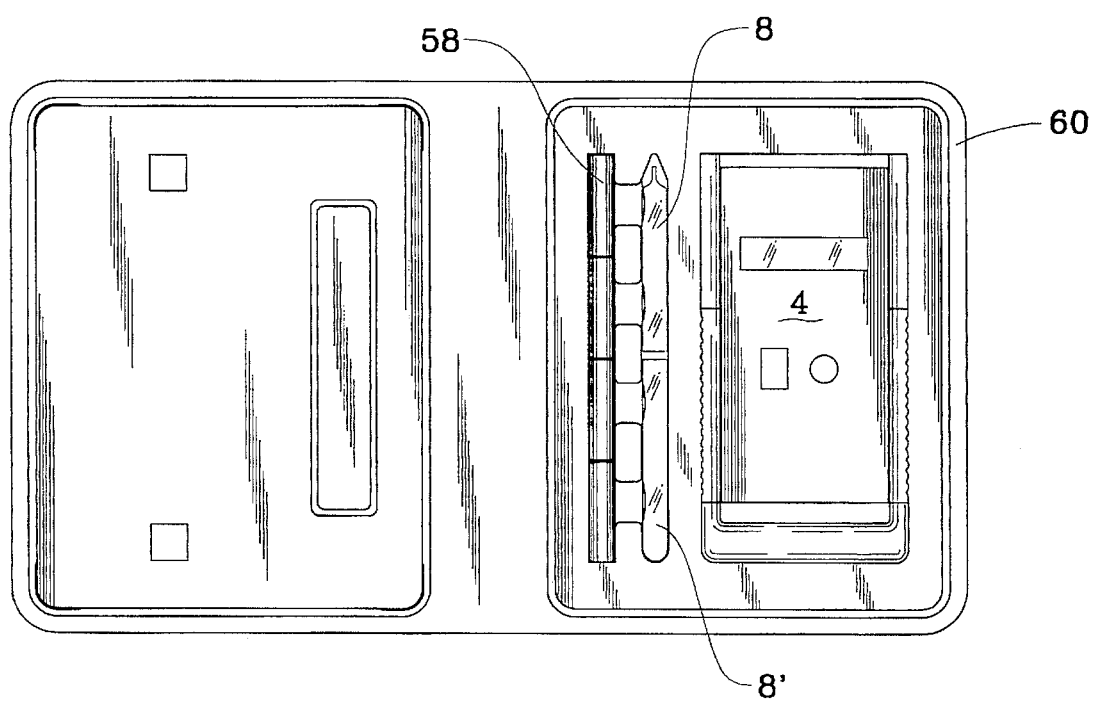
FIG. 5 is a perspective of an instrument module in accordance with the invention.

FIG. 5 shows an instrument module that comprises an instrument 4, a standardizing ampoule 8 containing liquid, an empty standardizing test tube 8', and a set of batteries 58 for the instrument. These items are conveniently transported in a folding case 60, which provides receptacles for them. The standardizing test tube 8', which also has a machine-readable bar code thereon, may be used to provide sample blank standardization to eliminate the effect of colored sample on the analytical results in known manner.

In use, filter assembly 12 is taken from the kit 40 and inserted into the receptacle 10 of the instrument. A standardizing ampoule 8, having a bar code 52 and alignment stripe 54 thereon, is inserted in the sample receptacle. The insertion of these two items activates the electronics of the instrument by way of the switches 18, and the instrument is caused to initiate a start-up/standardizing routine. The instrument identifies the ampoule as a standardizing ampoule by reading the code 52. The instrument then performs a known standardizing routine. The stripe 54 is used by the operator to align the ampoule so that the code 52 is aligned with the code reader 8. The instrument need not be re-standardized for about one hour under normal conditions.

After the instrument has been standardized for one analytical test procedure, the liquid sample being tested is placed in the sample cup 42 and pre-treated in a known manner. An analytical test ampoule is then inserted, tip down, into the sample cup, and the tip is broken off causing the sample to flow into the ampoule. After mixing the sample with the reagents in the ampoule, the ampoule is placed in the receptacle 6, and the instrument automatically detects the amount of light passing through the sample, compares that with an internally recorded relationship between received light and concentration, and displays the results on the instrument display 56.

In a preferred arrangement, each analysis kit includes one of approximately twenty-seven filter assemblies. Each filter element passes wavelengths selected from one of seven different wavelength bands.

Modifications within the scope of the appended claims will be apparent to those of skill in the art.

We claim:

1. A filter assembly for use in automatic chemical analysis comprising:

optical filter means for passing only selected frequencies of light appropriate for a selected chemical analysis and adapted to be received by a photometric instrument for conducting said selected chemical analysis, and readable code means affixed to said optical filter means and having thereon a code readable by said instrument, said code corresponding to said selected chemical analysis to be performed, for selecting said selected chemical analysis to be made on the basis of said code.

2. An assembly according to claim 1 wherein said optical filter means comprises an optical filter element and said assembly further comprises a holder for holding said element, and said readable code means is on said holder.

3. An assembly according to claim 2 in combination with a standardizing ampoule for use with said photometric instrument, said standardizing ampoule having a code thereon for being read by said photometric instrument and indicating that it is a standardizing ampoule.

4. A kit comprising an assembly according to claim 2 and further comprising at least one sample ampoule adapted to be received by said photometric instrument, said sample ampoule having analytical reagents therein.

5. A kit according to claim 4 further comprising a sample cup for receiving a sample to be tested, said sample ampoule being adapted to receive said sample from said sample cup.

6. Apparatus for performing automated chemical analysis comprising sample receptacle means for receiving a sample to be analyzed, means for illuminating said sample with a beam of light, means for receiving an optical filter assembly means for passing only selected frequencies of said beam of light, means for detecting the amount of said selected frequencies passed by said sample, means for providing an output indicative of said automated chemical analysis, and means for reading a code on said optical filter assembly means corresponding to the analysis to be performed and for selecting the analysis to be made on the basis of said code.

7. A combination according to claim 6 further comprising a plurality of said optical filter assembly means, each of which is designed to be used for a selected chemical analysis and contains a said code that is unique to said filter assembly.

8. A combination according to claim 6 in further combination with a standard ampoule for removable placement in said sample receptacle means and having a standard sample therein, said standard ampoule comprising means forming a code readable by said apparatus and identifying said standard ampoule.

9. A combination according to claim 7 in further combination with at least one sample ampoule for removable replacement in said sample receptacle means and for receiving a sample to be analyzed.

10. An instrument module comprising:

a photometric instrument for performing automated chemical analysis, said instrument comprising sample receptacle means for receiving a sample to be analyzed, means for illuminating said sample with a beam of light, means for receiving optical filter assembly means for passing only selected frequencies of said beam of light, means for detecting the amount of said selected frequencies passed by said sample, means for providing an output indicative of said analysis, means for reading a code on said optical filter assembly means corresponding to the analysis to be performed and selecting the analysis to be made on the basis of said code, and means for reading a machine readable code on a standardizing ampoule when said standardizing ampoule is inserted in said sample receptacle means, said standardizing ampoule for being received in said sample receptacle, said standardizing ampoule having said machine readable code thereon identifying said standardizing ampoule, and means for containing said instrument and said standardizing ampoule.

11. A method for conducting a photometric chemical analysis comprising providing a photometric instrument, providing an optical filter assembly for passing selected frequencies of light and having a machine readable code thereon, providing a sample ampoule for receiving a sample to be tested, inserting said optical filter assembly into a filter assembly receptacle in said instrument, inserting said sample ampoule into a sample ampoule receptacle in said instrument, reading said machine readable code, and automatically conducting an analytical test in response to said insertion steps by selecting a particular relationship between detected light and sample concentration as a function of said machine readable code.

12. A method according to claim 11 further comprising providing a standardizing ampoule having a second machine readable code thereon, inserting said standardizing ampoule in said sample ampoule receptacle, reading said second machine readable code on said standardizing ampoule, and automatically initiating a standardizing routine in response to reading said second machine readable code on said standardizing ampoule.

\* \* \* \* \*